US005080904A

United States Patent [19]
Iga et al.

[11] Patent Number: 5,080,904
[45] Date of Patent: Jan. 14, 1992

[54] LIPOSOME COMPOSITION AND ITS PRODUCTION

[75] Inventors: Katsumi Iga, Suita; Naoru Hamaguchi, Ibaraki; Yasuaki Ogawa, Otokuni, all of Japan

[73] Assignee: Takeda Chemical Industries, Ltd., Osaka, Japan

[21] Appl. No.: 350,030

[22] Filed: May 10, 1989

[51] Int. Cl.$^5$ ............................................. A61K 37/22
[52] U.S. Cl. .................................... 424/450; 264/4.3; 435/89
[58] Field of Search .................. 424/450; 435/89; 264/4.3

[56] References Cited

U.S. PATENT DOCUMENTS

| | | | |
|---|---|---|---|
| 4,619,913 | 10/1986 | Luck et al. | 514/801 |
| 4,782,019 | 11/1988 | Kokusho et al. | 435/89 |
| 4,818,537 | 4/1989 | Guo | 424/450 |
| 4,837,028 | 6/1989 | Allen | 424/450 |
| 4,880,634 | 11/1989 | Speiser | 424/450 |

*Primary Examiner*—Thurman Page
*Assistant Examiner*—William E. Benston, Jr.
*Attorney, Agent, or Firm*—Wenderoth, Lind & Ponack

[57] ABSTRACT

The liposome compositions entrapping a drug are prepared by constituting the liposomal membrane with a saturated phospholipid and a glycolipid having sulfo group. Thus obtained compositions circulate stably in blood for a long time after intravenous administration.

9 Claims, 3 Drawing Sheets

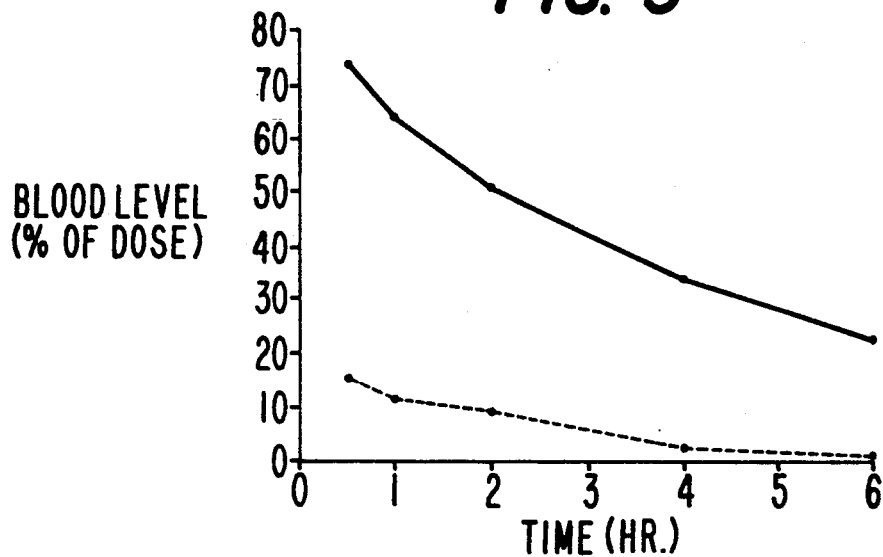
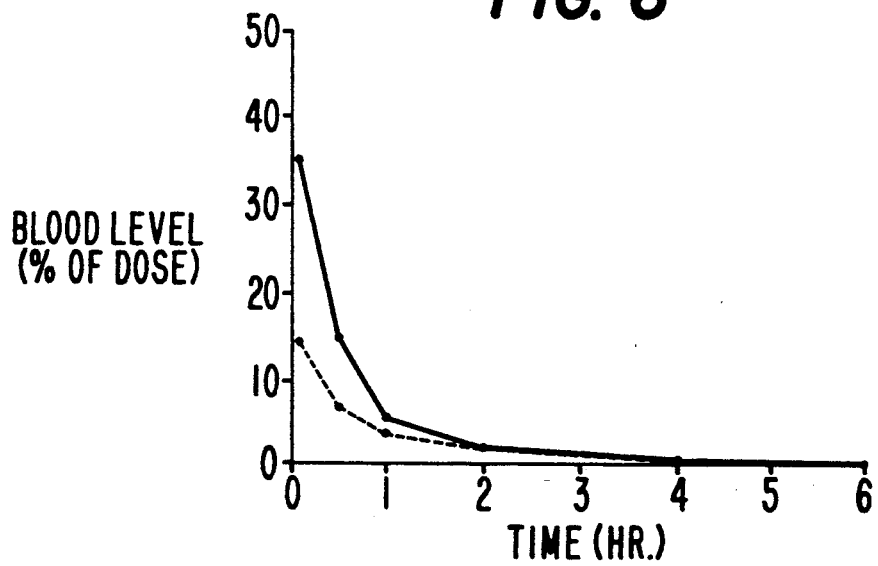

LIPOSOME COMPOSITION AND ITS PRODUCTION

The present invention relates to liposome compositions and the method of their production.

Drug delivery systems (DDS) have already been routinized in which a drug-entrapping liposome composition is intravenously administered and delivered to a particular target site in the subject's body [G. Gregoriadis et al.; Receptor-mediated Targeting of Drugs, Plenum Press, New York, pp. 243-266 (1980)].

The primary requirement of such DDS is that the liposome composition, after being intravenously administered, should stably circulate along with blood in the subject's body for a longer period of time than provided by conventional systems. Liposome, in essence, is not very stable in blood due to interaction between its membrane component lipid and blood components such as lipoprotein. Also, intravenously administered liposome is likely to be recognized as a foreign substance by the reticuloendothelial system (RES) and thus likely to disappear from blood due to its physical morphology and biochemical properties. This is why the disappearance rate of intravenously administered liposome is higher than expected. It has therefore long been an important problem how liposome in blood should be stabilized to avoid recognition by RES and thus to delay its disappearance from blood. For example, one paper reports a case where cholesterol was added to liposome membrane composition to increase blood liposome stability [C. G. Knight; Liposomes: From physical structure to therapeutic applications," Elsevier, North Holland, pp. 310-311 (1981)]. However, the effect thus obtained can be said to vary widely depending on the original membrane composition of the liposome [Biochemica et Biophysica Acta, 839, 58 (1985)]. Another paper reports that liposome delivery to RES can be suppressed by coating the surface of the liposome membrane with sialic acid using a glycoprotein having sialo group [Chemical and Pharmaceutical Bulletin, 34, 2979-2988 (1986)]. It is also reported that such sialic acid-containing glycolipid, when administered as liposome, is distributed to the liver, a part of RES [Biochemica et Biophysica Acta, 497, 760-765 (1977)]. It is also reported that a drug was delivered into the brain after increasing the liposome's ability to pass through the blood brain barrier (BB barrier) using sulfatide, a glycolipid with sulfo group [Biochemistry International, 9, 267-272 (1984); Japanese Published Unexamined Patent Application No. 146710/1982]. That is, the liposome prepared using sulfatide as a component became significantly highly capable of passing through the BB barrier unlike the sulfatide-free control liposome. However, drug distribution to the liver, an organ that provides an index of drug distribution in RES, tended to expand with sulfatide addition. This effect of sulfatide resulted from a combination of natural phosphatidylcholine with unsaturated acyl group and cholesterol for the membrane composition.

There has not yet been developed an effective and highly practical means of retarding liposome disappearance from blood following intravenous administration by modifying the liposome membrane composition.

In light of these conditions, the present inventors conducted investigations with the aim of modifying liposome membrane composition by adding a membrane modifier to make intravenously administered liposomes circulate stably with blood in the subject's body for longer periods, and developed the present invention.

Accordingly, the present invention provides: (1) a liposome composition entrapping a drug in liposome of which membrane is constituted by a phospholipid of which acyl groups are saturated acyl groups and a glycolipid having sulfo group, and (2) a method of producing a liposome composition entrapping a drug, which comprises (i) preparing an emulsion or a suspension containing a phospholipid of which acyl group are saturated acyl groups and a glycolipid having sulfo group, wherein an effective amount of a drug is added, and (ii) subjecting the resulting emulsion or suspension to preparation of liposome vesicles so that the liposomal membrane is constituted by said phospholipid and glycolipid.

The phospholipids used to produce the liposome composition of the present invention are glycerophospholipids and sphingophospholipids, both having saturated acyl groups. Examples of such phospholipids include those whose two acyl groups are saturated alkyls having 8 or more carbon atoms, acyl groups at least one of which is a saturated alkyl group having 10 or more carbon atoms, preferably 12 to 18 carbon atoms. It is preferably to use a phospholipid whose saturated acyl groups are both saturated alkyls having 12 to 18 carbon atoms. Such phospholipids include hydrogenated lecithin as obtained by hydrogenation of animal/plant-derived lecithin (e.g. yolk lecithin, soybean lecithin), semi-synthetically or total-synthetically obtained phosphatidylcholine comprising a combination of lauroyl, myristoyl, palmitoyl, stearoyl, etc., phosphatidylethanolamine, phosphatidylserine, phosphatidylglycerol, phosphatidylinositol, and sphingomyelin. Specifically, examples include the following phospholipids, whose phase transition temperature (found value) is shown in parentheses: dimyristoylphosphatidylcholine (DMPC, 23.9° C.), palmitoylmyristoylphosphatidylcholine (PMPC, 27.2° C.), myristoylpalmitoylphosphatidylcholine (MPPC, 35.3° C.), dipalmitoylphosphatidylcholine (DPPC, 41.4° C.), stearoylpalmitoylphosphatidylcholine (SPPC, 44.0° C.), palmitoylstearoylphosphatidylcholine (PSPC, 47.4° C.), distearoylphosphatidylcholine (DSPC, 54.9° C.), dimyristoylphosphatidylethanolamine (DMPE, 50° C.), dipalmitoylphosphatidylethanolamine (DPPE, 60° C.), disteraroylphosphatidylethanolamine (DSPE, over 60° C.), dimyristoylphosphatidylserine (DMPS, 38° C.), dipalmitoylphosphatidylserine (DPPS, 51° C.), distearoylphosphatidylserine (DSPS, over 50° C.), dimyristoylphosphatidylglycerol (DMPG, 23° C.), dipalmitoylphosphatidylglycerol (DPPG, 41° C.), distearoylphosphatidylglycerol (DSPG, 55° C.), dipalmitoylsphingomyelin (DPSM, 41° C.) and distearoylsphingomyelin (DSSM, 57° C.). These phospholipids may be used singly or in combination.

Examples of the glycolipid with sulfo group used in the liposome composition of the present invention include sulfate-containing sulfatosphingoglycolipids such as sulfatide [phase transition temperature=34.8° C./47.3° C.; Biochemica et Biophysica Acta, 859, 246-256 (1986)] and lactosylsulfatide; and sulfate-containing sulfatoglyceroglycolipids such as seminolipid and sulfoglyceroglycolipid. Sulfatide is especially preferable.

In the present invention, the liposome membrane is composed of a phospholipid and a glycolipid, as described above.

The mixing ratio of phospholipid and glycolipid for the present invention is normally about 0.5 to 50 parts by weight, preferably about 2 to 20 parts by weight of glycolipid to 100 parts by weight of phospholipid.

The desired liposome membrane is prepared so that it would have a phase transition temperature of about 37° to 60° C., preferably about 40° to 55° C. Phase transition temperature can be adjusted by choosing an appropriate type of phospholipid and glycolipid, mixing ratio, etc.

Since the phase transition temperature of a liposome composition is generally near the theoretical value obtained by proportionally distributing the phase transition temperatures of respective constituent lipids to weight [cf. C. G. Knight; "Liposomes: From physical structure to therapeutic applications," Elsevier, North Holland, pp. 310–311 (1981)], it is possible to choose a lipid composition to obtain the desired membrane phase transition temperature on the basis of this relationship.

Usually, membrane phase transition temperature can be adjusted so that it falls in the above-mentioned range using a mixing ratio as shown above; the purpose of the present invention can thus be accomplished, i.e., the disappearance of the obtained liposome composition from blood is retarded. In preparing the desired liposome composition, stabilizers such as antioxidants and other additives (e.g. sugars serving as osmotic pressure regulators) may be used as long as they do not interfere with the purpose of the invention.

The present invention is characterized by the use of a phospholipid and glycolipid as described above to compose a liposome membrane; known technique are used to produce the desired liposome composition. For example, the above liposome membrane composition containing a phospholipid with saturated acyl group and a glycolipid with sulfo group is dissolved in an organic solvent such as diethyl ether, isopropyl ether or chloroform, and then emulsified with an aqueous solution of a drug to give a W/O type emulsion; the organic solvent is then evaporated under reduced pressure over 40° C. to yield reverse-phase evaporation vesicles (REV). It is also possible to obtain multilamellar vesicles (MLV) by mixing at a temperature exceeding 40° C. a drug solution and a film prepared by evaporating the organic solvent from the above lipid solution therein. MLV may be shaken using a probe type ultrasonic shaker to yield small unilamellar vesicles (SUV). Other methods of producing liposomes include the stable plurilamellar vesicle method (Japanese Published Unexamined Patent Application No. 500952/1984) and the dehydration-rehydration vesicle method [C. Kirby et al.; Biotechnology, Nov., 979 (1984)]. The glycolipid with sulfo group can also be used in dispersion in drug aqueous solution in place of in solution in organic solvent. It is also possible to use the method in which a drug-entrapping liposome composition is prepared using a phospholipid with saturated acyl group and added to a dispersion containing a glycolipid with sulfo group, followed by mixing while heating, to place the glycolipid with sulfo group on the already formed liposome membrane.

In cases where a fat-soluble drug with low water solubility is used, it may be dissolved in a lipid solution in organic solvent as mentioned above to give a liposome composition containing the drug. The drug-entrapping liposome composition thus obtained can be adjusted to a preferable particle size as needed. Although this liposome composition can be used directly, it is preferable to used it after separating and removing the free portion of the drug not entrapped therein, e.g., by centrifugation, gel filtration or dialysis.

There is no particular limitation on the choice of a drug for the present invention, as long as the drug is used to compose a DDS; a hydrophilic or lipophilic drug or mixture thereof can be used. Examples of drugs which can be used include antitumor agents such as platinum compounds [cisplatin and its derivatives (e.g. carboplatin, spiroplatin)], adriamycin, mitomycin C, actinomycin, ansamitocin, bleomycin, 5-FU and methotrexate; lymphokines such as natural or recombinant interferons ($\alpha$, $\beta$, $\gamma$) and natural or recombinant interleukin 2; physiologically active peptides such as manganese superoxide dismutase (SOD) and its derivative superoxide dismutase PEG (PEG-5000) (Japanese Published Unexamined Patent Application No. 16685/1983); antifungal drug such as amphotericin B, $\beta$-lactum antibiotics such as sulfazecin; aminoglycoside antibiotics such as gentamycin, streptomycin and kanamycin; vitamins such as cyanocobalamin and ubiquinone; antiprotozoan drugs such a meglemine antimonate; enzymes such as alkaline phosphatase; anticoagulation agents such as heparin; antiallergic agents such as amlexanox; immunopotentiating agents such as muramyldipeptide, muramyltripeptide and TMD-66 [Gann., 74 (2), 192–195 (1983)]; and general drugs such as propranolol and glutathione.

The present invention is suitable for water-soluble drugs. Examples of such drugs include drugs having an octanol-water partition ratio below 10 in log value. An appropriate amount of drug entrapment is chosen with consideration of the type, effective dose etc. of the drug so that an effective amount is entrapped in the liposome.

The liposome composition of the present invention is generally used in the form of a solution or emulsion; it is dispersed in physiological saline, phosphate-buffered physiological saline etc. in amounts chosen as appropriate to the purpose of the treatment, and intravenously administered by injection or drip infusion.

The liposome composition of the present invention circulates along with blood in the subject's body stably for long periods following intravenous administration; the toxicity intrinsic to the drug entrapped therein is thus modified, and the drug targeting effect for a particular lesion is enhanced. Therefore, the present liposome composition is useful for enhancing the sustained therapeutic effect of drugs. Particularly, the liposome composition of the present invention entrapping an antitumor agent is expected to have an improved therapeutic effect when administered in hyperthermia treatment of cancer; in this case, it is preferable to use a liposome composition having a membrane phase transition temperature of about 40° to 55° C.

BRIEF EXPLANATION OF THE DRAWINGS

FIGS. 1, 2, 3, 4 and 5 respectively show the relationship between elapsed time and blood drug concentration after intravenous administration to rats of the liposome compositions obtained in Examples 1, 2, 3, 4 and 6. FIG. 6 shows the time course of blood concentration of the liposome composition obtained by the method of Experimental Example 1-1. In these figures, -------●------- represents changes in blood concentration of the drug prepared in the absence of sulfatide. Values of blood concentration are expressed in percent ratio to dose, and 10% of body weight was taken as the total amount of blood.

Figure 1:
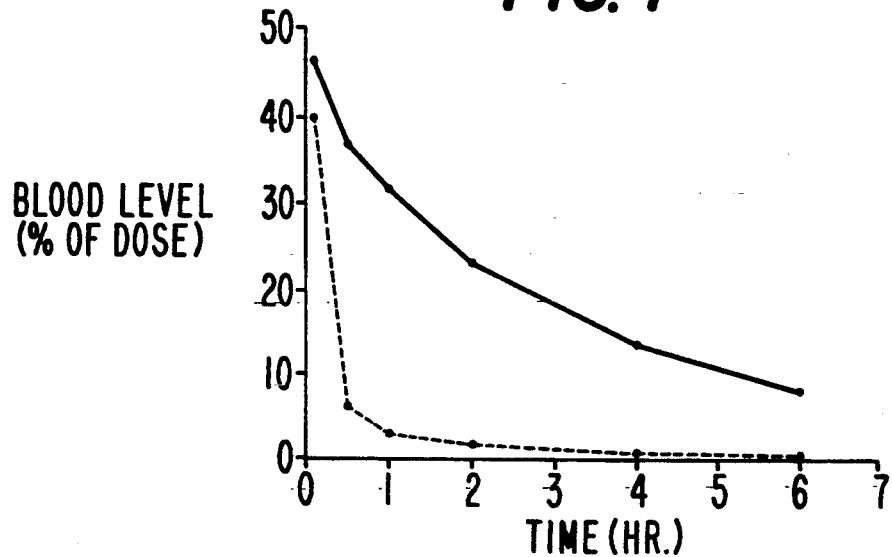

The present invention will now be described in more detail by means of the following working examples, test examples and experimental examples. Note that the sulfatide used in these examples was extracted and purified from bovine brains.

Phase transition temperature was determined by differential thermal analysis.

EXAMPLE 1

270 mg of DPPC, 30 mg of DSPC and 30 mg of sulfatide were dissolved in 70 ml of a 1:1 mixed solution of chloroform and isopropyl ether in a 1 l beaker. To this solution was added 10 ml of a 6-carboxyfluorescein (6-CF) solution, pH 7, prepared so that it had the same osmotic pressure as physiological saline. This mixture was emulsified using a probe-type ultrasonic shaker (Ohtake) to yield a W/O type emulsion. Ultrasonication at 50 W for 30 seconds was repeated 10 times. The emulsion thus obtained was placed in a rotary evaporator and the organic solvent was distilled off at 60° C. under reduced pressure to yield REV. The evaporator was adjusted so that the degree of vacuum decreased as the organic solvent evaporated to prevent bumping. The small amount of organic solvent that remained in REV was then distilled off while blowing nitrogen gas. The obtained REV was diluted to 10 ml with an appropriate amount of physiological saline, filtered through a 1.2-micron filter (Acrodisc, Gelman), and dialyzed with a dialysis membrane (Spectrapor, Spectrum Medical) against physiological saline for 24 hours to yield a 6-CF-entrapping liposome composition. Quantitative determination of liposome-entrapped 6-CF (Note 1) revealed a 6-CF entrapment ratio of 22.4%. The liposome membrane had a phase transition temperature of 42.1° C.

(Note 1) Quantitative determination of 6-CF in liposome and calculation of entrapment ratio 0.1 ml of liposome was diluted 100-fold with a phosphate-buffered physiological saline (PBS, pH 7.2) and further diluted 100-fold with PBS containing 0.02% Triton X-100, followed by heating for 30 minutes at 60° C. to destroy the liposome. The fluorescence intensity of the solution was measured (Hitachi F3000 fluorospectrometer, excitation wavelength=494 nm, determination wavelength=515 nm) to determine the total 6-CF content in the liposome dispersion. Separately, 0.1 ml liposome was diluted 10000-fold with PBS; a 2.5-ml portion of this dilution was filtered through a centrifugal filter (Centrisart, SM 13249E, Sartorius); the fluorescence intensity of the resulting filtrate was measured to determine the amount of unentrapped free 6-CF that remained in the liposome dispersion.

Entrapment ratio =

$$\frac{\text{(total 6-CF content in liposome)} - \text{(free 6-CF content in liposome)}}{\text{(amount of 6-CF used to prepare the liposome)}} \times 100$$

EXAMPLE 2

The procedure of Example 1 was followed, but 15 mg of sulfatide was used in place of 30 mg of sulfatide, to yield a liposome composition entrapping 6-CF at a 23.3% entrapment ratio and having a 42.4° C. phase transition temperature.

EXAMPLE 3

The procedure of Example 1 was followed, but 45 mg of sulfatide was used in place of 30 mg of sulfatide, to yield a liposome composition entrapping 6-CF at a 18.9% incorporation ratio and having a 42.4° C. phase transition temperature.

EXAMPLE 4

The procedure of Example 1 was followed, but 210 mg of DPPC and 90 mg of DSPC were used in place of 270 mg of DPPC and 30 mg of DSPC, to yield a liposome composition entrapping 6-CF at a 29.1% entrapment ratio and having a 41.7° C. phase transition temperature.

EXAMPLE 5

The procedure of Example 1 was followed, but sulfatide was not dissolved in a mixed solution of chloroform and isopropyl ether but dispersed in the 6-CF solution, to yield a liposome composition entrapping 6-CF at a 18.8% entrapment ratio and having a 42.1° C. phase transition temperature.

EXAMPLE 6

360 mg of DPPC, 40 mg of DSPC and 40 mg of sulfatide were dissolved in 40 ml of chloroform in a 1 l beaker. The organic solvent was distilled off using a rotary evaporator to form a lipid film on the glass wall. The trace amount of organic solvent that remained in the film was removed by blowing nitrogen gas. The film thus prepared, together with 10 ml of a 6-CF solution as used in Example 1 maintained at 60° C., was subjected to vortex treatment at 60° C. to yield MLV. This MLV was ultrasonicated at 50 W power using the probe-type ultrasonic shaker used in Example 1 for about 10 minutes to yield SUV, which was then filtered and dialyzed in the same manner as Example 1 to yield a liposome composition entrapping 6-CF at a 5.5% entrapment ratio and having a 42.1° C. phase transition temperature.

EXAMPLE 7

The procedure of Example 6 was followed, but 280 mg and 120 mg of DSPC were used in place of 360 mg of DPPC and 40 mg of DSPC, to yield a liposome composition entrapping 6-CF at a 6.0% entrapment ratio and having a 42.1° C. phase transition temperature.

EXAMPLE 8

The procedure of Example 6 was followed, but 400 mg of DSPC was used in place of both 360 mg of DPPC and 40 mg of DSPC, to yield a liposome composition entrapping 6-CF at a 7.0% entrapment ratio and having a 52.9° C. phase transition temperature.

EXAMPLE 9

Sulfatide-free MLV, in place of MLV that contains sulfatide as a membrane component, was prepared using the same conditions as in Example 6. 10 ml of physiological saline containing 40 mg of dispersed sulfatide was added to this MLV, followed by mixing at 60° C. for about 30 minutes to yield MLV having sulfatide spiked in its membrane. The procedure of Example 6 was then followed to yield a liposome composition entrapping 6-CF at a 4.5% entrapment ratio and having a 42.1° C. phase transition temperature.

EXPERIMENTAL EXAMPLE 1-1

Sulfatide-free liposomes corresponding to respective liposomes obtained in the above Examples 1, 2, 3, 4 and 6 were prepared. Also the procedure of Example 1 was followed, but 250 mg of egg yolk lecithin, 40 mg of cholesterol and 40 mg of sulfatide were used in place of 270 mg of DPPC, 30 mg of DSPC and 30 mg of sulfatide, to yield a liposome composition. A sulfatide-free liposome composition corresponding to this liposome composition was then prepared.

EXPERIMENTAL EXAMPLE 1-2

Figure 2:
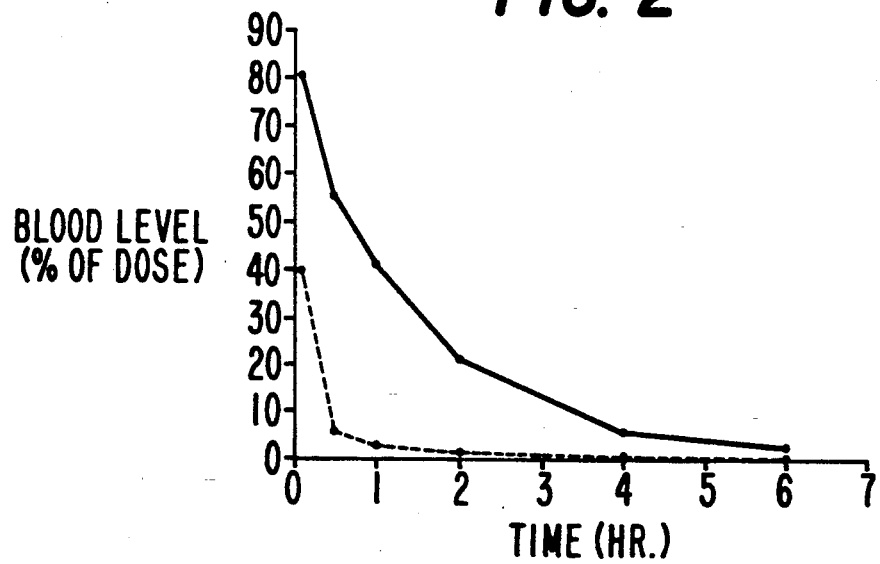
Figure 3:
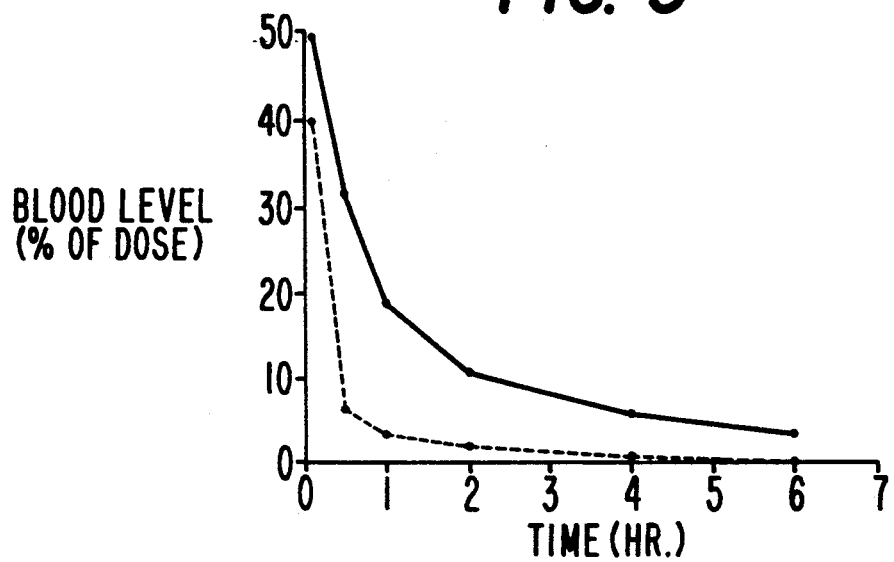
Figure 4:
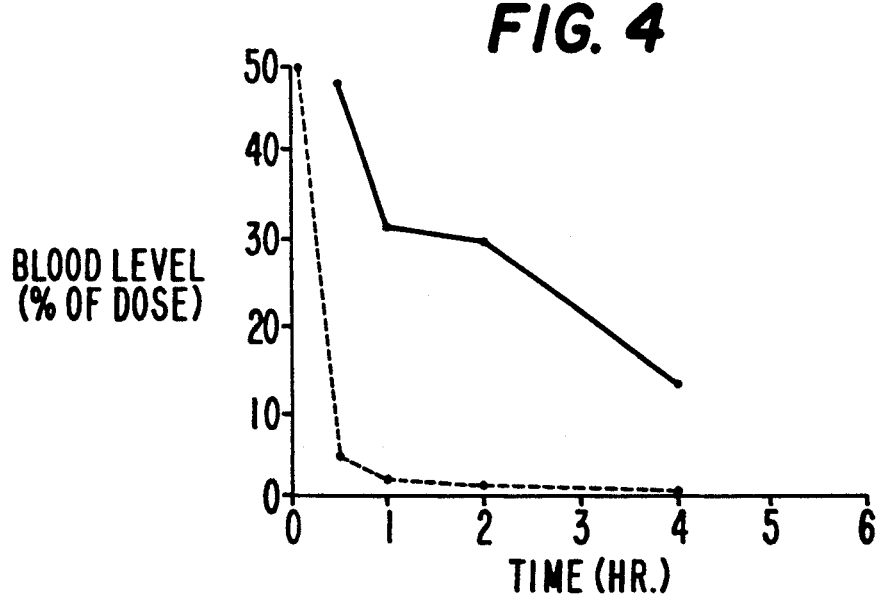

The liposome compositions obtained in Examples 1, 2, 3, 4 and 6 and similarly prepared sulfatide-free liposome compositions were each intravenously administered to rats in amounts of 0.1 to 0.5 ml, and disappearance of liposome from blood was monitored (Note 2). The results shown in FIGS. 1 through 5 were obtained. As seen in these figures, the sulfatide-containing liposomes maintained blood 6-CF concentrations higher than those of sulfatide-free control liposomes 1, 2, 4 and 6 hours after administration, with mean values of increase rate at 11.4, 14.6, 15.2 and 20.9 times, respectively. On the other hand, as seen in FIG. 6, the disappearance of 6-CF in the sulfatide-containing liposome prepared from egg yolk lecithin and cholesterol was found to be as rapid as that of the control liposome. As demonstrated by these results, the method of liposome production of the present invention, using a phospholipid with saturated acyl group and a glycolipid with sulfo group, can be judged efficient and highly practicable for retarding liposome disappearance from blood after its intravenous administration.

EXPERIMENTAL EXAMPLE 1-3

The liposome compositions used in Experimental Example 1-2 were each intravenously administered to rats. One hour later, liver 6-CF concentration was measured to determine liposome dispersion in RES (Note 2). The results obtained are shown in Table 1. These results demonstrate that liposome disappearance from blood was retarded and liposome distribution in the liver and other RES organs was reduced.

TABLE 1

6-CF Concentration (%) in the Liver,
Determined One Hour after Administration

| Liposome type | With sulfatide | Without sulfatide |
|---|---|---|
| Example 1 | 8.0 | 30.1 |
| Example 2 | 7.2 | 30.1 |
| Example 3 | 7.6 | 30.1 |
| Example 4 | 12.4 | 59.7 |
| Example 6 | 14.2 | 44.7 |
| Egg Yolk lecithin-cholesterol | 32.3 | 33.9 |

(Note 2) Methods of determining blood and liver 6-CF liposome concentrations

A blood dispersion was prepared by adding 10 ml PBS of 0.2 ml of heparin-treated tail vein blood. This dispersion was centrifuged (3,000 rpm, 10 min). To 5 ml of the resulting supernatant, 0.05 ml of Triton X-100 was added, followed by heating at 60° to 70° C. to destroy the liposome. The fluorescence intensity of the released 6-CF was measured to determine the blood liposome concentration. Also, a liver excised after laparotomy and exsanguination was immersed in PBS containing 0.02% Triton X-100 to yield 100 ml, then disrupted using a tissue homogenizer (Polytron, Kinematica), after which it was heated at 60° to 70° C. so that 6-CF releases from the liposome in the homogenate. This homogenate was ultracentrifuged (50,000 g, 10 min), diluted 20- to 50-fold, and filtered through a 0.45-micron membrane filter (Acrodisk, Gelman). The fluorescence intensity was then measured to determine liver liposome concentration.

EXPERIMENTAL EXAMPLE 1-4

The liposome compositions obtained in Examples 1, 2, 3 and 4 and corresponding sulfatide-free liposome compositions were each diluted 10,000-fold with PBS. The thermal drug release property of these dilutions was determined by continuously measuring 6-CF released from liposomes using a fluorometer connected to the heating system in order to monitor the phase change (from gel to liquid crystal) in the liposome membranes. The thermal release initiation temperatures determined on release curves are shown in Table 2.

TABLE 2

Liposome Membrane Phase Transition Temperature (°C.)
and Temperature (°C.) of Initiation of 6-CF Thermal Release
from Liposomes

| Liposome Type | Phase Transition Temp. | Thermal Release Initiation Temp. |
|---|---|---|
| Example 1 (with sulfatide) | 42.1 | 37.2 |
| Example 2 (with sulfatide) | 42.4 | 37.0 |
| Example 3 (with sulfatide) | 41.7 | 35.5 |
| Example 1, 2, 3, but without sulfatide | 42.8 | 39.0 |
| Example 4 (with sulfatide) | 44.5 | 37.2 |
| Example 4, but without sulfatide | 45.5 | 38.4 |

EXAMPLE 10

The procedure of Example 1 was followed, but a 500 μg/ml cisplatin (CDDP) solution in physiological saline was used in place of a 6-CF solution, to yield a liposome composition entrapping CDDP at a 21.5% entrapment ratio and having a 42.1° C. phase transition temperature. (Note 3) Method of determining CDDP content in liposome 0.1 ml of liposome was dispersed in 0.5 ml of physiological saline; 2.5 ml of the dispersion was frozen and heated; about 2.5 ml of the obtained disrupted liposome solution was filtered through Centrisalt. To 0.1 ml of the resulting filtrate 2 ml of a 0.1N NaOH solution containing 10% diethyl dithiocarbamate (DDTC) was added, and this mixture was left at room temperature for 30 minutes. The resulting adduct was extracted with 5 ml of n-hexane; the extract was assayed by HPLC (column, Zorbax CN; eluent, n-hexane/isopropyl alcohol=8/2; UV=250 nm) to determine the total CDDP content of the liposome dispersion. Separately, the approx. 2.5 ml portion of liposome dispersion that remained was filtered through Centrisalt, followed by the above procedure to yield an adduct, and the free CDDP not entrapped in the liposome in the dispersion was quantified.

EXAMPLE 11

The procedure of Example 10 was followed, but a mixed solution of 25 mM 6-CF and 250 μg/ml CDDP was used in place of the CDDP solution, to yield a liposome composition entrapping 6-CF and CDDP at respective entrapment ratios of 18.2% and 17.6% and having a 42.1° C. phase transition temperature.

EXAMPLE 12

The procedure of Example 10 was followed, but 15 mg of sulfatide was used in place of 30 mg of sulfatide, to yield a liposome composition entrapping CDDP at a 18.4% entrapment ratio and having a 42.4° C. phase transition temperature.

EXAMPLE 13

The procedure of Example 11 was followed, but 15 mg of sulfatide was used in place of 30 mg of sulfatide, to yield a liposome composition entrapping 6-CF and CDDP at respective entrapment ratios of 16.5% and 16.2% and having a 42.4° C. phase transition temperature.

EXAMPLE 14

The procedure of Example 10 was followed, but 45 mg of sulfatide was used in place of 30 mg of sulfatide, to yield a liposome composition entrapping CDDP at a 19.4% entrapment ratio and having a 41.7° C. phase transition temperature.

EXAMPLE 15

The procedure of Example 11 was followed, but 45 mg of sulfatide was used in place of 30 mg of sulfatide, to yield a liposome composition entrapping 6-CF and CDDP at respective entrapment ratios of 17.6% and 16.8% and having a 41.7° C. phase transition temperature.

EXAMPLE 16

The procedure of Example 10 was followed, but 210 mg of DPPC and 90 mg of DSPC were used in place of 270 mg of DPPC and 30 mg of DSPC, to yield a liposome composition entrapping CDDP at a 23.4% entrapment ratio and having a 44.5° C. phase transition temperature.

EXAMPLE 17

The procedure of Example 11 was followed, but 210 mg of DPPC and 90 mg of DSPC were used in place of 270 mg of DPPC and 30 mg of DSPC, to yield a liposome composition entrapping 6-CF and CDDP at respective entrapment ratios of 21.7% and 18.1% and having a 44.5° C. phase transition temperature.

EXAMPLE 18

The procedure of Example 10 was followed, but a solution of CDDP in physiological saline was used in place of the 6-CF solution used in Example 6 to yield a liposome composition entrapping CDDP at a 6.2% entrapment ratio and having a 42.1° C. phase transition temperature.

EXAMPLE 19

The procedure of Example 11 was followed, but a mixed solution of 6-CF and CDDP was used in place of the CDDP solution used in Example 18, to yield a liposome composition entrapping 6-CF and CDDP at respective entrapment ratios of 5.8% and 4.5% and having a 42.1° C. phase transition temperature.

EXAMPLE 20

The procedure of Example 14 was followed, but 280 mg of DPPC and 120 mg of DSPC were used in place of 360 mg of DPPC and 40 mg of DSPC, to yield a liposome composition entrapping CDDP at a 7.4% entrapment ratio and having a 44.5° C. phase transition temperature.

EXAMPLE 21

The procedure of Example 20 was followed, but a mixed solution of 6-CF and CDDP was used in place of the CDDP solution used in Example 20, to yield a liposome composition entrapping 6-CF and CDDP at respective entrapment ratios of 6.2% and 4.9% and having a 44.5° C. phase transition temperature.

EXPERIMENTAL EXAMPLE 2-1

Liposome compositions were prepared in the same manner as in Examples 11, 13, 17 and 19, but sulfatide was not added.

EXPERIMENTAL EXAMPLE 2-2

The liposome compositions obtained in Examples 11, 13, 17 and 19 and sulfatide-free liposome compositions respectively corresponding thereto were each intravenously administered to rats in amounts of 0.1 to 0.5 ml, and liposome disappearance from blood was monitored by measuring blood 6-CF concentration during the 6-hour period following the administration. The sulfatide-containing liposomes maintained blood concentrations higher than those of sulfatide-free control liposome compositions 1, 2, 4 and 6 hours after administration, with mean values of increase rate at 8.5, 19.7, 16.4 and 28.5 times, respectively. Also, blood CDDP concentration was measured during the 1-hour period following the administration (Note 4); it was as high as 6-CF concentration, suggesting that CDDP, together with 6-CF, was entrapped in the liposomes in blood. As demonstrated by these results, the method of liposome production of the present invention, which uses a phospholipid with saturated acyl group and a glycolipid with sulfo group, can be judged to be efficient and highly practicable for retarding liposome disappearance from blood after its intravenous administration.

(Note 4) Method of determining blood CDDP concentration

A blood dispersion was obtained by adding 2 ml PBS to 0.2 ml of heparin-treated tail vein blood, followed by centrifugation. To 1 ml of the separated supernatant was added 1 ml of a DDT solution, and the total CDDP content in blood was determined using the above procedure for CDDP determination.

EXAMPLE 22

The procedure of Example 1 was followed, but a 308 μg protein/ml interleukin 2 (IL-2) aqueous solution (solution type: 25 mM ammonium acetate solution, pH 6) was used in place of the 6-CF solution, to yield a liposome composition entrapping IL-2 at a 24.4% entrapment ratio (Note 6) and having a 42.1° C. phase transition temperature. Note that free IL-2 in the liposomes was separated by centrifugation (Sorvall, at 50,000 g, for 30 minutes).

(Note 6) Method of determining IL-2 content in liposomes

To IL-2-entrapping liposomes ultracentrifugated to remove free IL-2, an equal amount of a 0.4% (V/V) Triton X-100 aqueous solution was added, followed by incubation at 7° C. for 30 minutes to disrupt the liposomes. The released IL-2 or ultracentrifugally separated supernatant was assayed by HPLC (column, Ultrapore; UV=210 nm) on a density gradient. The HPLC eluents used were a solution of 0.1% (V/V) trifluoroacetic acid in acetonitrile/water (40/60 V/V) (Eluent A) and another solution of 0.1% (V/V) trifluoroacetic acid in acetonitrile/water (65/35 V/V) (Eluent B); gradient elution was conducted using the following conditions:

| Time | Eluent A | Eluent B |
|---|---|---|
| 0 min. | 90% | 10% |
| 20 min. | 0% | 100% |
| 25 min. | 0% | 100% |
| 30 min. | 90% | 10% |

Flow rate: 0.9 ml/min.

EXAMPLE 23

The procedure of Example 22 was followed, but a mixed solution of 25 mM 6-CF and 154 μg protein/ml IL-2 was used in place of the IL-2 solution, to form a liposome composition entrapping 6-CF and IL-2 at respective entrapment ratios of 19.0% and 18.5% and having a 42.1° C. phase transition temperature.

EXPERIMENTAL EXAMPLE 3-1

A liposome composition was prepared in the same manner as Example 23, but sulfatide was not added.

EXPERIMENTAL EXAMPLE 3-2

The liposome composition of Example 23 and corresponding sulfatide-free liposome composition were each intravenously administered to rats in amounts of 0.1 to 0.5 ml, and liposome disappearance from blood was monitored by measuring blood 6-CF concentration during the 6-hour period following the administration. The sulfatide-containing liposome composition maintained a blood concentration higher than that of the sulfatid-free control liposome composition 1, 2, 4 and 6 hours after administration, with means values of increase rate at 10.9, 11.0 15.3 and 14.7, respectively. As demonstrated by these results, the method of liposome production of the present invention, using a phospholipid with saturated acyl group and a glycolipid with sulfo group, can be judged to be efficient and highly practicable for retarding liposome disappearance from blood after its intravenous administration.

EXAMPLE 24

The procedure of Example 1 was followed, but a 100 μ/ml ansamitocin solution in physiological saline was used in place of the 6-CF solution, to yield a liposome composition entrapping ansamitocin and having a 42.1° C. phase transition temperature.

EXAMPLE 25

The procedure of Example 1 was followed, but a 5 mg/ml methotrexate solution in physiological saline was used in place of the 6-CF solution, to yield a liposome composition entrapping methotrexate and having a 42.1° C. phase transition temperature.

EXAMPLE 26

The procedure of Example 1 was followed, but a 200 μg/ml mitomycin C solution in physiological saline was used in place of the 6-CF solution, to yield a liposome composition entrapping mitomycin C and having a 42.1° C. phase transition temperature.

EXAMPLE 27

The procedure of Example 1 was followed, but a 1 mg/ml adriamycin solution in physiological saline was used in place of the 6-CF solution, to yield a liposome composition entrapping adriamycin and having a 42.1° C. phase transition temperature.

EXAMPLE 28

The procedure of Example 1 was followed, but a 3 mg/ml bleomycin solution in physiological saline was used in place of the 6-CF solution, to yield a liposome composition entrapping bleomycin and having a 42.1° C. phase transition temperature.

What is claim is:

1. A liposome composition entrapping a drug in liposome of which membrane is constituted by a phospholipid of which the acyl groups thereof are saturated acyl groups and a glycolipid selected from the group consisting of sulfate-containing sulfatosphingoglycolipids, lactosylsulfatides and sulfate-containing sulfatoglyceroglycolipids, said drug being selected from the groups consisting of antitumor agents, lymphokines, physiologically active peptides, antibiotics, vitamins, antiprotozoan drugs, enzymes, anticoagulation agents, antiallergic agents or immunopotentiating agents and wherein said phospholipid has two acyl groups which are saturated alkyls having 8 or more carbon atoms, acyl groups at least one of which is a saturated alkyl group having 10 or more carbon atoms and wherein said glycolipid is present in an amount of 0.5 to 50 parts per 100 parts by weight of said phospholipid.

2. The composition according to claim 1, wherein the sulfate-containing sulfatosphingoglycolipid is sulfatide.

3. The composition according to claim 1, wherein the phospholipids are glycerophopholipids or sphingophospholipids.

4. The composition according to claim 1, wherein phase transition temperature of the liposomal membrane is in the range of about 40° to 55° C.

5. The composition according to claim 1, wherein the drug is for drug delivery systems.

6. The composition according to claim 1, wherein the antitumor agents are platinum compounds.

7. The composition according to claim 1, wherein the platinum compound is cisplatin.

8. The composition according to claim 1, wherein the drug is the antitumor agent selected from the group consisting of platinum compounds, adriamycin, mitomycin C, antinomycin, ansamitocin, bleomycin, 5-FU and methotrexate and the phase transition temperature of the liposomal membrane is in the range of about 40° to 55° C.

9. The composition according to claim 8, wherein the platinum compound is one or more selected from the group consisting of cisplatin, carboplatin and spiroplatin.

* * * * *